(12) United States Patent
Udrea et al.

(10) Patent No.: US 10,527,571 B2
(45) Date of Patent: Jan. 7, 2020

(54) CMOS-BASED SEMICONDUCTOR DEVICE ON MICRO-HOTPLATE AND METHOD OF FABRICATION

(71) Applicant: AMS SENSORS UK LIMITED, Cambridge (GB)

(72) Inventors: Florin Udrea, Cambridge (GB); Syed Zeeshan Ali, Cambridge (GB); Julian Gardner, Cambridge (GB)

(73) Assignee: AMS SENSORS UK LIMITED, Cambridgeshire (GB)

( * ) Notice: Subject to any disclaimer, the term of this patent is extended or adjusted under 35 U.S.C. 154(b) by 498 days.

(21) Appl. No.: 15/123,630

(22) PCT Filed: Feb. 27, 2015

(86) PCT No.: PCT/GB2015/050568
§ 371 (c)(1),
(2) Date: Sep. 2, 2016

(87) PCT Pub. No.: WO2015/132563
PCT Pub. Date: Sep. 11, 2015

(65) Prior Publication Data
US 2017/0074815 A1 Mar. 16, 2017

(30) Foreign Application Priority Data
Mar. 5, 2014 (GB) .................................. 1403868.1

(51) Int. Cl.
*G01N 27/00* (2006.01)
*G01N 27/04* (2006.01)
(Continued)

(52) U.S. Cl.
CPC ............. *G01N 27/04* (2013.01); *G01N 27/14* (2013.01); *G01N 33/0027* (2013.01);
(Continued)

(58) Field of Classification Search
None
See application file for complete search history.

(56) References Cited

U.S. PATENT DOCUMENTS 5,464,966 A 11/1995 Gaitan
7,963,147 B2 6/2011 Jun et al.
(Continued)

FOREIGN PATENT DOCUMENTS

DE 4400838 A1 7/1995
GB 2321336 A 7/1998
(Continued)

OTHER PUBLICATIONS

Office Action from corresponding Chinese Application No. 201580011862.7, dated Jul. 4, 2018.
(Continued)

*Primary Examiner* — Bradley Smith
(74) *Attorney, Agent, or Firm* — Tucker Ellis LLP; M. David Galin (57) ABSTRACT

It is disclosed herein a semiconductor device and a method of manufacturing the semiconductor device. The semiconductor device is made using partly CMOS or CMOS based processing steps, and it includes a semiconductor substrate, a dielectric region over the semiconductor substrate, a heater within the dielectric region and a patterned layer of noble metal above the dielectric region. The method includes the deposition of a photoresist material over the dielectric region, and patterning the photo-resist material to form a patterned region over the dielectric region. The steps of depositing the photo-resist material and patterning the photo-resist material may be performed in sequence using similar photolithography and etching steps to those used in a CMOS process. The resulting semiconductor device is then subjected to further processing steps which ensure that a dielectric membrane and a metal structure within the
(Continued)

membrane are formed in the patterned region over the dielectric region.

18 Claims, 9 Drawing Sheets

(51) Int. Cl.
| | |
|---|---|
| *G01N 27/14* | (2006.01) |
| *H05B 3/26* | (2006.01) |
| *H05B 3/14* | (2006.01) |
| *G01N 33/00* | (2006.01) |
| *H01L 21/8238* | (2006.01) |

(52) U.S. Cl.
CPC ............... *H05B 3/143* (2013.01); *H05B 3/26* (2013.01); *H05B 3/265* (2013.01); *H01L 21/8238* (2013.01); *H05B 2203/013* (2013.01); *H05B 2203/017* (2013.01)

(56) References Cited

U.S. PATENT DOCUMENTS

| | | |
|---|---|---|
| 2003/0039586 A1 | 2/2003 | Toyoda |
| 2004/0075140 A1 | 4/2004 | Baltes |
| 2009/0126460 A1* | 5/2009 | Gardner ............. G01N 33/0031 73/31.06 |
| 2011/0174799 A1 | 7/2011 | Zeeshan |
| 2012/0267532 A1 | 10/2012 | Udrea |

FOREIGN PATENT DOCUMENTS

| | | |
|---|---|---|
| GB | 2422017 A | 7/2006 |
| JP | H0634591 A | 2/1994 |
| JP | H08278274 A | 10/1996 |
| JP | 2006194853 A | 7/2006 |
| JP | 2007171207 A | 7/2007 |
| JP | 2011112642 A | 6/2011 |
| JP | 2013239401 A | 11/2013 |
| WO | 9519563 A1 | 7/1995 |
| WO | 02/50528 A1 | 6/2002 |
| WO | 2007/026177 A1 | 3/2007 |
| WO | 2013/167874 A1 | 11/2013 |

OTHER PUBLICATIONS

Office Action from corresponding Taiwanese Application No. 104106622, dated Jun. 22, 2018.
Graf, Markus et al., "CMOS microhotplate sensory system for operating temperatures up to 500° C.", Sensors and Actuators B Chemical, Oct. 2006, pp. 346-352.
Graf, Markus et al., "CMOS Monolithic Metal-Oxide Sensory System Comprising a Microhotplate and Associated Circuitry", IEEE Sensors Journal, Feb. 2004, vol. 4, No. 1, pp. 9-16.
Office Action from corresponding Japanese Application No. 2016-555644, dated Oct. 16, 2018.
Graf, M. et al., "CMOS Microhotplate Sensor System for Operating Temperatures Up to 500° C.," Sensors and Actuators B Chemistry, vol. 117, No. 2, Oct. 12, 2006, pp. 346-352.
Graf, M. (Identified by Baltes, H. on corresponding International Search Report) et al., "CMOS Monolithic Metal-Oxide Sensor System Comprising a Microhotplate and Associated Circuitry," IEEE Sensors Journal, vol. 4, No. 1, Feb. 1, 2004, pp. 9-16.
Search Report from Corresponding GB Application No. GB1403868. 1, dated Sep. 8, 2014.
Ali, S. Z., "Tungsten-Based SOI Microhotplates for Smart Gas Sensors", J. Microelectromechanical Systems, 2008, 17, 6, pp. 1408-1417.
Iwaki, T., "Design and Simulation of Resistive SOI CMOS Microheaters for High Temperature Gas Sensors", J. Phys. Conference series, 2005, 15, pp. 27-32.
Afridi, M. "A Monolithic CMOS Microhotplate-Based Gas Sensor System", IEEE Sensors, 2002, 2, 6, pp. 644-655.
Udrea, F., "Design and Simulations of SOI CMOS Micro-Hotplate Gas Sensors", Sensors and Actuators B, 2001, 78, pp. 180-190.
Dibbern, U., "A Substrate for Thin-Film Gas Sensors in Microelectronics Technology", Sensors and Actuators B, 2, 1990, pp. 63-70.
Stankova, M. et al., "Detection of SO2 and H2S in CO2 stream by means of WO3-based micro-hotplate sensors," Sensors and Actuators B Chemical, 102, 2004, pp. 219-225.
Baroncini, M. et al., "Thermal characterization of a microheater for micromachined gas sensors," Sensors and Actuators B Chemical, 115, 2004, pp. 8-14.
Simon, I. et al., "Micromachined metal oxide gas sensors: opportunities to improve sensor performance," Sensors and Actuators B Chemical, 73, 2001, pp. 1-26.
Suehle, J.S., et al., "Tin Oxide Gas Sensor Fabricated Using CMOS Micro-Hotplates and In-Situ Processing," IEEE Electron Device Letters, vol. 14, No. 3, Mar. 1993, pp. 118-120.
Parameswaran, M. et al., "Micromachined Thermal Radiation Emitter from a Commercial CMOS Process," IEEE Electron Device Letters, vol. 12, No. 2, Feb. 1991, pp. 57-59.
San, H. et al., "A silicon micromachined infrared emitter based on SOI wafer," MEMS/MOEMS Technologies and Applications III, 2007, 8 pages.
Daly, J.T. et al., "Nano-Structured Surfaces for Tuned Infrared Emission for Spectroscopic Applications," In Micro-and Nano-photonic Materials and Devices, 2000, pp. 80-89.
Chang, Yi-Tsung et al., "Emission properties of Ag/dielectric/Ag plasmonic thermal emitter with different lattice type, hole shape, and dielectric material," Applied Physics Letters, 95, 21313, 2009, 4 pages.
International Search Report and Written Opinion from corresponding International Patent Application No. PCT/GB2015/050568, dated May 11, 2015.
Communication Pursuant to Rule 114(2) EPC from corresponding European Patent Application No. 15707746.2, dated Dec. 14, 2018, 4 pages.
Cambridge CMOS Sensors Ltd., CMOS MEMS Micro-Hotplates: Minature micro-hotplates for the next generation of micro and nano sensing applications, Copyright 2013, 4 pages.
Cambridge CMOS Sensors Ltd., CMOS MEMS Micro-Hotplates: Minature micro-hotplates with on-chip circuit integration for micro and nano sensing applications, Copyright 2013, 4 pages.
Cambridge CMOS Sensors Ltd., CCSMHx09x MEMS Microhotplate, v3.2, 2013, 2 pages.
Andon Electronics Corporation, Andon Interconnection Specialists, Sockets—Cambridge CMOS Sensors Ltd., Oct. 17, 2013, 1 page.

\* cited by examiner

CMOS-BASED SEMICONDUCTOR DEVICE ON MICRO-HOTPLATE AND METHOD OF FABRICATION

FIELD OF THE INVENTION

This invention relates to a device and a method of manufacturing a semiconductor device, based on micro-hotplates, particularly but not exclusively, for gas sensors. The invention also relates to Infra-Red (IR) sources and the manufacturing method of such sources based on CMOS technology.

BACKGROUND OF THE INVENTION

It is known to fabricate micro-hotplate structures on a silicon substrate. Such structures consist of a micro-heater embedded within a thin dielectric membrane, typically consisting of silicon dioxide and/or silicon nitride.

Such structures can be used for resistive gas sensors, by having electrodes on top, onto which a gas sensitive material is deposited. For example, U. Dibbern et. al, "A substrate for thin-film gas sensors in microelectronic technology," Sensors and Actuators B, 1990 describes the design of a micro-hotplate using NiFe alloy as a heater material, in an oxy-nitride membrane. The device has electrodes on top and is used for gas sensing. Similarly M. Stankova et. al, "Detection of $SO_2$ and $H_2S$ in $CO_2$ stream by means of $WO_3$-based micro-hotplate sensors" Sensors and Actuators B, 2004 describes micro-hotplates based on a polysilicon heater within an oxy-nitride membrane. M. Baroncini et. al., "Thermal characterization of a microheater for micromachined gas sensors," describes a gas sensor with a micro-heater made from platinum.

Similarly, many such reports can be found in literature using micro-hotplate devices for gas sensors. Reference to some of these are given in I. Simon et. al, "Micromachined metal oxide gas sensors: opportunities to improve sensor performance," Sensors and Actuators B (2001), and S. Z. Ali Et. Al, "Tungsten-Based SOI Microhotplates for Smart Gas Sensors" Journal of MEMS 2008.

Most of these reported devices are not fabricated in a standard microelectronics technology. The microelectronics technology is today referred to in a generic form as CMOS technology as this is the technology to fabricate Integrated circuits.

The CMOS term is well known in microelectronics field. In its wide meaning, it refers to the silicon technology for making integrated circuits. CMOS ensures very high accuracy of processing identical transistors (up to billions), high volume manufacturing, very low cost and high reproducibility at different levels (wafer level, wafer to wafer, and lot to lot). CMOS comes with high standards in quality and reliability.

There are many books and articles describing CMOS and there are many variants of CMOS technologies and devices that can be fabricated using CMOS technology. A very basic reference to CMOS can be found in Wikipedia (https://en.wikipedia.org/wiki/CMOS):

"Complementary metal-oxide-semiconductor (CMOS) is a technology for constructing integrated circuits. CMOS technology is used in microprocessors, microcontrollers, static RAM, and other digital logic circuits. CMOS technology is also used for several analogue circuits such as image sensors (CMOS sensor), data converters, and highly integrated transceivers for many types of communication. Frank Wanlass patented CMOS in 1963 (U.S. Pat. No. 3,356,858). Besides digital applications, CMOS technology is also used in analogue applications. For example, there are CMOS operational amplifier ICs available in the market. Transmission gates may be used instead of signal relays. CMOS technology is also widely used for RF circuits all the way to microwave frequencies, in mixed-signal (analogue and digital) applications."

Today CMOS processes exist in large microelectronics foundries, most of which are accessible to customers (i.e. can be accessed by more than one company, legal entity or individual). Such processes come with warranties and can be deployed in extremely large volumes.

Not all silicon technologies are CMOS technologies. Examples of non-CMOS technologies are given below:
- Lab technologies (as opposed to foundry technologies) which are not deployable in volume and are not used for fabrication of a large number of transistors, but are specialised, used in low volume (such as those for R&D)
- Screen printing technologies
- Bio-technologies as for example those employed in making fluidic channels
- MEMS technologies, such as those used for accelerometers or gyroscopes
- Very high voltage vertical power device technologies, such as Vertical Bipolar Junction Transistor technologies
- Technologies that use materials which are not CMOS compatible, such as gold, platinum or radioactive materials.

It is worth mentioning that some of the technologies listed above as non-CMOS can in some cases be employed in post-CMOS or pre-CMOS processes without affecting the CMOS processes.

As already mentioned, most of the sensors are not fabricated in CMOS technology and many are not compatible with CMOS technology. For example, platinum is used as a heater in some of the previously mentioned reports, but is not available as a material in CMOS processes. CMOS technology offers many advantages such as low fabrication cost in high volume, possibility of circuit integration on the same chip, and good reproducibility from device to device. These advantages are not available if incompatible materials or processes are used.

There are some reports of CMOS based micro-hotplates. For example, Suehle et. al. "Tin Oxide Gas Sensor Fabricated Using CMOS Micro-hotplates and In-Situ Processing," IEEE Electron Device Letters 1993, F. Udrea et. al. "Design and simulations of SOI CMOS micro-hotplate gas sensors," Sensors and Actuators B 2001, M. Afridi Et. al, "A monolithic CMOS Microhotplate-Based Gas Sensor System," IEEE Sensors Journal 2002, U.S. Pat. No. 5,464,966, M. Graf "CMOS microhotplate sensor system for operating temperature up to 500° C." Sensors and Actuators B 2005, S. Z. Ali Et. Al, "Tungsten-Based SOI Microhotplates for Smart Gas Sensors" Journal of MEMS 2008, all report different examples of micro-hotplates fabricated in CMOS technology. Other reports by these same groups give information on similar devices, using polysilicon, MOSFETs, Single Crystal Silicon, and tungsten as heater materials.

One critical aspect for resistive gas sensors is the fabrication of the electrodes on top of the membrane which are used to measure the resistance of the sensing material. Ideally these electrodes should be made from a noble metal such as gold or platinum. However, both of these metals are usually not available in a CMOS process. As a result, one option is to use a metal available in CMOS, such as aluminium, which has been reported in Suehle et. al. "Tin Oxide Gas Sensor Fabricated Using CMOS Micro-hotplates and In-Situ Processing," IEEE Electron Device Letters 1993. However, aluminium forms aluminium oxide on its surface, and as a result does not make a good electrical contact with the sensing material.

Another option is to deposit gold or platinum in a separate post-CMOS process. This allows the devices to have good contact to the sensing material while having a CMOS process. However, this step is not as straight forward as it seems. One possible method is to fabricate the device in CMOS and bulk etch it to release the membrane. Then spin photoresist on the wafer, and pattern using an appropriate mask, followed by sputtering or evaporation of the required metal.

However, this results in low yield and poor manufacturability because the photoresist coating and patterning can damage the membranes. Indeed the membranes are very thin (<10 μm), so when a photoresist is spun at high speed, there is likelihood that the membranes can break. The vacuum on the photoresist spinners can also cause membranes to break. Additionally, the fabricated membranes are often slightly bent due to residual stresses within the membrane layers. This can result in an uneven distribution of the photoresist, and also cause the mask patterns to be less well defined.

In addition, in general most foundries as well as lithography equipment are equipped and designed to work with standard wafers, and are not designed for working with wafers that have membranes. For example some mask aligners use a vacuum from the front side to pick up the wafer, which in the case of membrane wafers can cause several membranes to break. As a result of all these reasons, it is very difficult to deposit gold in this method on the micro-hotplates.

The other way to deposit is by performing the bulk etching after the patterning and deposition of the electrodes. For example M. Graf et. al. "CMOS microhotplate sensor system for operating temperature up to 500° C." Sensors and Actuators B 2005 use this method to deposit the platinum electrodes. In this way, the patterning and gold deposition is done on a standard wafer, and the back etching step is done later. The problem with this method is that the platinum deposited on the wafer can contaminate the equipment used for the bulk etching.

M. Afridi Et. al, "A monolithic CMOS Microhotplate-Based Gas Sensor System," IEEE Sensors Journal 2002, use a slightly different but similar process. In their process, after the CMOS processing, they deposit gold on the entire wafer, and then spin a resist on it and pattern it. The wafer is then bulk etched to release the membrane (a suspended membrane in this case). This is then followed by etching the gold to remove it from the regions where it is not required.

Using this method, the advantage is that no lithography or spinning is required on the wafers after bulk etching, so there are no problems with the handling of membranes in the lithography machines. However, similar to the method used by Graf, it still means that the wafers that are put in the machine for bulk etching already contain gold, and so can contaminate the machine. Additionally, the described device is a suspended membrane, which is mechanically less stable.

IR emitters are also well known. For example, Parameswaran et. al. "Micro-machined thermal emitter from a commercial CMOS process," IEEE EDL 1991, and San et. al. "A silicon micromachined infra-red emitter based on SOI wafer" (Proc of SPIE 2007), describe IR emitter devices based on micro-hotplates on either suspended bridges or membranes.

To improve the emission of the IR emitters, often materials are deposited on top. This can be a coating of a high emissivity material, such as carbon, or metal blacks, or can be plasmonic structures. Plasmonic structures, such as those described by J. Daly "Nano-Structured Surfaces for Tuned Infrared Emission for Spectroscopic applications", Micro- and Nano-photonic Materials and Devices, 2000, or by Y. Chang "Emission properties of Ag/dielectrid/Ag plasmonic thermal emitter with different lattice type, hole shape, and dielectric material," Applied Physics letters 213102, 2009, can improve IR emission for certain wavelengths. These consist of one or more layers on the top surface specially designed in a repeating pattern.

These plasmonic structures can be made from gold or platinum, and their deposition method faces the same challenges as for the electrodes for the resistive gas sensors.

It is an object of the present invention to address the problems discussed above.

STATEMENT OF THE INVENTION

In accordance with one aspect of the present invention there is provided a method of manufacturing a microhotplate comprising a semiconductor substrate, a dielectric region over the semiconductor substrate, a resistive heater within the dielectric region, the method comprising: forming the semiconductor substrate, the dielectric region, and the resistive heater using complementary metal oxide semiconductor, CMOS, compatible processing steps; depositing a photo-resist material over the dielectric region using the CMOS compatible processing steps; patterning the photo-resist material to form a patterned region over the dielectric region using the CMOS compatible processing steps; subsequently etching at least a portion of the semiconductor substrate to form a dielectric membrane, wherein the steps of depositing the photo-resist material, patterning the photo-resist material and etching the portion of the semiconductor substrate are performed in sequence; and subjecting the dielectric membrane to a further process which ensures that a metal structure is deposited in the patterned region over the dielectric region.

It is disclosed herein a microhotplate comprising: a semiconductor substrate having an etched portion; a dielectric region over the semiconductor substrate; a resistive heater formed within the dielectric region; and a patterned metal layer formed over the dielectric region. The semiconductor substrate, the dielectric region, the resistive heater and the patterned metal layer are formed using the method described above.

In accordance with a further aspect of the present invention, there is provided a microhotplate comprising: a semiconductor substrate having an etched portion; a dielectric region over the semiconductor substrate; a resistive heater formed within the dielectric region; and a patterned metal layer formed over the dielectric region. The semiconductor substrate, the dielectric region, the resistive heater are formed using a CMOS compatible technique. A pattern for the patterned metal layer is defined by the CMOS compatible technique, and the etched portion in the substrate is formed using an etching technique and the patterned metal layer is formed using a further technique.

Further aspects and preferred features are set out in claim 2 et seq.

It will be appreciated that the dielectric region may include one or more dielectric layers. When the resistive heater is incorporated within the dielectric region, one dielectric layer may present in both sides of the resistive heater. The term "CMOS compatible process" covers the processing steps used within a CMOS process as well as covers certain processing steps performed separately from the CMOS process, but utilising processing tools usable in the CMOS processing steps. For example, the processing steps of forming the substrate, dielectric region and resistive heater inside the dielectric region are performed within the CMOS processing steps, and the processing steps of depositing the photoresist material and patterning the photoresist material can be performed separately (outside the CMOS processing steps) using photolithography tools which are also usable in the CMOS process. Alternatively, the term "CMOS compatible process" covers the processing steps in which the substrate, dielectric region, resistive heater inside the dielectric region and the patterned photoresist material are formed using directly the CMOS process (or within the CMOS processing steps). The term "dielectric membrane" refers to the device structure in which the semiconductor structure is back etched. The dielectric membrane structure generally includes the etched substrate, dielectric region on the etched substrate, resistive heater and interconnects within the dielectric region and patterned photoresist over the dielectric region. The dielectric membrane structure is subjected to the metal deposition step which is performed in a process which is generally not CMOS compatible (post CMOS process or a non-CMOS process).

The invention generally provides a semiconductor device and a method of manufacturing the semiconductor device. The semiconductor device is made using partly CMOS or CMOS based processing steps, and it comprises a semiconductor substrate and at least one first dielectric layer over the semiconductor substrate, a heater, and at least one second further dielectric layer over the heater and at least one patterned layer of noble metal above the at least one further dielectric layer. The method comprises the deposition of a photo-resist material over the said second dielectric layer of the semiconductor structure; patterning the photo-resist material to form a patterned region over the dielectric layer. The steps of depositing the photo-resist material, patterning the photo-resist material are performed in sequence using similar photolithography and etching steps to those used in CMOS. The resulting semiconductor device is then subjected to further processing steps which ensure that a dielectric membrane and a metal structure within the membrane are formed in the patterned region over the second dielectric layer.

The membrane is formed by back-side etching, preferably by Deep Reaction Ion Etching (DRIE) after all the CMOS and the CMOS like steps have been completed.

The noble metal structure may be a layer of gold or platinum and is deposited preferably after the dielectric membrane is formed. Alternatively, the metal structure may be a discrete structure made of gold or platinum. It will be appreciated that the noble metal structure can be generally used as a pair of interdigitated electrodes so that the semiconductor device can act as a gas sensor, in which case a further chemically sensitive layer is formed above the pair of interdigitated electrodes. The metal structure may be used as a plasmonic structure in an IR source. In both these applications, a resistive heater is embedded between the first and the second dielectric layers (or within the dielectric region) and placed within the dielectric membrane so that the semiconductor structure can operate as a gas sensor and/or an IR emitter. Since the semiconductor device incorporates the resistive heater within the dielectric membrane, it can be referred as a microhotplate. The semiconductor device refers to a structure made with CMOS processing steps or CMOS like steps, which includes the photoresists patterning of the noble metal, followed by deep etching of at least part of the substrate to form the membrane, the noble metal deposition and lift-off using the previously patterned photoresist. The back-side etching, the noble metal deposition and lift-off are referred to as non CMOS or post CMOS processing steps. By non CMOS or post CMOS processing steps we refer generally to steps that are not used in the state-of-the-art CMOS processing steps due to the lack of CMOS control and the tolerances associated with the CMOS steps and/or the possibility of contamination of the tools. For example both Gold and Platinum can act as deep dopants or traps in the semiconductor band gap which could affect the performance of any other CMOS based devices or circuits.

The noble metal layer is deposited preferably by sputtering or evaporation. The lift-off process comprises removing the photo-resist material and the part of the metal layer on top of the photo-resist material so that the metal structure formed in the patterned region is retained over the said second dielectric layer. The photo-resist material and the metal structure on top of the photo-resist material are removed using a chemical solution and/or a chemical solvent.

Whilst much of the above description has made reference to a lift-off technique, it will be appreciated by one skilled in the art that it is conceivable to use a chemical solvent and/or a solution (so as to remove photo-resist and a material on top of the photo-resist) under conditions other than ones which would normally be used as part of a lift-off technique.

In preferred embodiments, it is disclosed a micro-hotplate suspended on a dielectric membrane formed using back-side etching that would use at least one metal layer made of gold or platinum which is patterned using photolithography within the CMOS process as one of the last steps of the CMOS processing sequence or using CMOS like steps for photolithography and etching, while the metal deposition by sputtering or evaporation and the subsequent lift-off process to define the metal patterns are done post CMOS and advantageously after the dielectric membrane formation by back-side etching is accomplished. Thus, within the CMOS process or in a similar fashion to that used in the CMOS process, the photoresist may be spun on the wafer and patterned by standard photolithography which may give the precision and the reproducibility specific to CMOS processes. The next step may be to carry out a back-side etching, preferably using Deep Reactive Ion Etching (DRIE) to release the dielectric membrane. After this, one or more of the metal structures above are deposited by sputtering or evaporation and further made into desired patterns by the lift-off process.

The step of patterning the photo-resist material may comprise applying a mask to define the patterned region over the dielectric layer. The step of patterning the photo-resist material may comprise using a photolithography tool within the CMOS processing steps to define the patterned region over the dielectric layer. The step of etching the semiconductor substrate may comprise applying a mask adjacent to the back of the semiconductor substrate (i.e. not the side of the semiconductor substrate above which the noble metal structure is formed) to define the portion of the semiconductor substrate to be etched. The step of etching the semiconductor substrate may comprise applying a Deep Reactive Ion Etching, DRIE, technique.

After the etching of the substrate and prior to depositing the metal structures, the method may further comprise depositing one or more adhesive or diffusion barrier layers on top of the photo-resist layer and in the patterned region over the dielectric layer. The adhesive or diffusion barrier layers may be a sandwich of metals to avoid problems such as lack of adhesion or undesirable diffusion of noble metal atoms into the dielectric layers. For example a gold layer can have chromium and/or nickel underneath or could be made in conjunction with a titanium layer.

In further embodiments, the final fabricated device may be a resistive gas sensor, partly fabricated in a CMOS technology, with either a bulk silicon starting wafer or a silicon-on-insulator (SOI) wafer. The difference between the bulk silicon wafer and the SOI wafer is that the bulk silicon wafer does not have any buried oxide formed within the device structure. In one embodiment, the heater may be made of polysilicon, aluminium, single crystal silicon, a MOSFET, or a high temperature CMOS metal, for example tungsten or titanium or a combination of those.

The shape of the metal structures or electrodes may be interdigitated, in circular or rectangular shape, or can be just two contacts next to each other, or can be spiral shaped, or may include concentric rings. It should be apparent that many different electrode shapes and designs can be contemplated by the skilled person.

Above the electrodes a chemical or gas sensitive layer is deposited by for example by screen printing, sputtering, chemical vapour deposition (CVD) ink-jet or drop coating. When this layer is exposed to a gas at a particular temperature controlled by the heater, a reaction or diffusion of the gas occurs modifying the electrical properties such as resistance (or capacitance) of the chemical or gas sensitive layer. This chemical or gas sensitive layer may be a conductive metal oxide such as tin oxide, zinc oxide, tungsten oxide or polymer based. The chemical or gas sensitive layer can be like a drop above the electrodes or, if thin enough (e.g. below 2 microns) can be conformal to the electrodes. Preferably this chemical or gas sensitive layer should be confined to the region above the said electrodes, to avoid stress and thermal dissipation which would increase the power consumption of the devices.

The dielectric membrane itself may be circular, rectangular, or rectangular shaped with rounded corners to reduce the stresses in the corners, but other shapes are possible as well. The top passivation of the device may be either silicon dioxide or silicon nitride.

The method may further include fabricating a temperature sensor embedded within the dielectric membrane. This may be a resistive temperature sensor made from a metal, or polysilicon, or single crystal silicon, or can be a diode. Preferably the diode may be made with the same CMOS layer used in the CMOS process to make transistors such as n-channel and p-channel FETs. This example is particularly relevant when the semiconductor structure includes a MOSFET structure manufactured using the CMOS processing steps. The cathode of the diode can therefore be formed by using the source of the drain layers of n-channel MOSFET while the anode of the diode can be formed by using the same source or drain layers of a p-channel MOSFET.

The device may also have a heat spreading plate made of metal or polysilicon, or in the case of Silicon on Insulator substrates, the device may have a single crystal silicon plate. The role of the spreading plate is to spread more uniformly the heat and thus improve the uniformity of the temperature in the heater area.

In further embodiments, there is provided a device and a method to fabricate an IR CMOS compatible emitter. This may be similar to the resistive gas sensor, and may include a heater embedded within the dielectric membrane to form as in the previous case, a micro-hotplate. In this case, instead of the electrodes onto which a sensitive layer is deposited for sensing the change in the resistance due to the gas presence, the top noble metal structure layer is patterned into plasmonic structures to increase the Infrared emissivity of the device. The plasmonic pattern refers to repeated (but not necessary regular) features of dots, holes, rectangles, trapezoid or other structures to enhance the IR radiation at particular wavelengths and/or reduce the infra-red radiation at other undesirable wavelengths, depending on the required emission spectrum. These plasmonic structures can therefore act as IR emissivity enhancers for some wavelengths and/or filters for others.

In embodiments, the method may integrate analogue or digital CMOS circuitry on the same chip (either the resistive gas sensor, or the IR emitter). This may be achieved because of the use of CMOS technology to fabricate the micro-hotplate. The circuitry may be a drive circuit for the heater, consisting of a simple current supply, for example using a current mirror circuit, or a more complex circuit to allow heater drive through a constant voltage, constant current or constant power circuit, or a PWM drive. There may also be circuitry to measure the temperature sensor in the membrane, and additionally using it to have a feedback loop to allow a constant temperature control of the heater. Bidirectional current drive can also be implemented.

Other circuitry may be read-out circuitry for the temperature sensor, or the sensing layer. This may include an amplifier, a filter, as well as an analogue to digital converter. Digital circuits may also be integrated to allow digital processing of the signal. Besides these, an off-membrane temperature sensor, based on a thermodiode, a resistive temperature sensor, or Vptat or Iptat circuits may also be integrated.

BRIEF DESCRIPTION OF THE PREFERRED EMBODIMENTS

Some preferred embodiments of the invention will now be described by way of example only and with reference to the accompanying drawings, in which.

DETAILED DESCRIPTION OF THE PREFERRED EMBODIMENTS

Embodiments of the invention describe a method of manufacturing a CMOS based micro-hotplate fabricated with gold or platinum electrodes deposited over the device structure. In this method, the device is fabricated in a state-of-the-art CMOS process. The process could be either bulk CMOS or SOI CMOS. The heater can be made using tungsten, polysilicon, a MOSFET, aluminium or single crystal silicon—all of these layers being CMOS compatible.

The micro-hotplate is then further processed by spinning and patterning a resist on the front side (near the resistive heater) of the wafer for the deposition of the gold electrodes, before the release of the membrane. The wafer is then back-etched using either dry etching through Deep Reactive Ion etching (DRIE) or wet etching using KOH. Gold or platinum is then sputtered on the front side to form the gold electrodes. Before one of these metal layers is deposited, it is possible that other layers of metals such as nickel, chromium or titanium are formed to improve adhesion and minimise diffusion into the dielectric layers or oxide layers. The process is completed when the lift-off is carried out to achieve the desired pattern (previously defined by the photolithography step in the CMOS)

Using this method, according to preferred embodiments, the lithography is performed on a wafer with standard thickness, without membranes, while at the same time, the metal deposition is done after the etching process, and so the etch equipment is not contaminated. Both Platinum and Gold are contaminants and so their use in CMOS or etch equipment is best avoided.

Preferably the back etch of the membrane is carried out using a Deep Reactive Ion Etch (DRIE). This results in vertical walls and hence reduced area consumption, and additionally good control of the final shape of the membrane, which in turn ensure high reproducibility across the wafer. Alternatively the membrane can be formed by wet etching using for example Potassium Hydroxide (KOH) or TetraMethyl Ammonium Hydroxide (TMAH). This results in a cheaper process.

In one embodiment, the device and the method described above are not limited to resistive gas sensors, but can be applied to other membrane based devices. According to a further embodiment, such a device and the method to produce it can be applied to CMOS based IR emitters.

Figure 1:
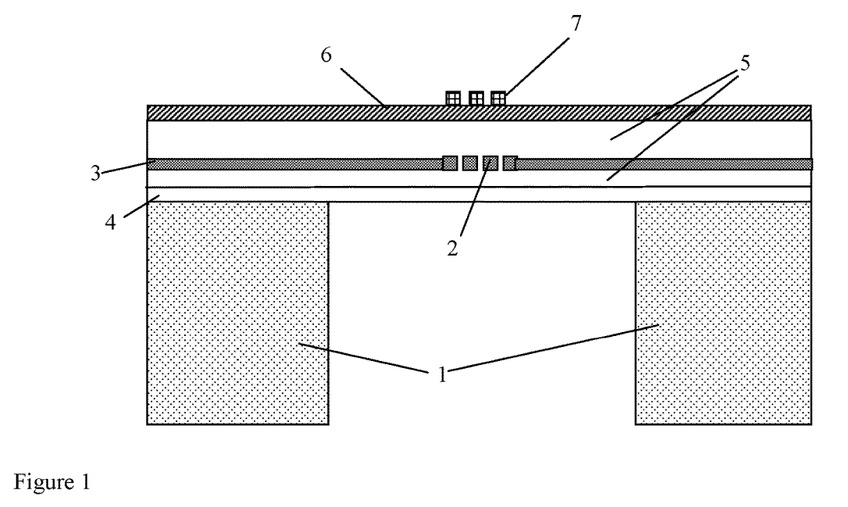
FIG. 1 illustrates a schematic cross-section of a micro-hotplate made in a CMOS SOI process with post processed electrodes for resistive gas sensing.

FIG. 1 shows the schematic cross-section of a micro-hotplate made in an SOI process with post processed electrodes for resistive gas sensing. The device consists of a silicon substrate 1 and a membrane consisting of buried oxide 4, dielectric layers 5 and passivation 6 which is supported by the substrate. A resistive heater 2 is embedded within the membrane, and tracks 3 are used to connect the heater to the pads. On top of the passivation there are electrodes 7 formed of either gold or platinum which can be used to make contact to the sensing material. The etching is done by deep reactive ion etching (DRIE) to achieve near vertical sidewalls of the trench. The heater 2 is made within the CMOS sequence. The photolithography of the electrodes 7 is done as one of the last steps of the CMOS sequence and before the DRIE. The final pattern of the electrodes 7 is finalised by a lift-off technique (using the photolithography step done within the CMOS) after the DRIE. It will be appreciated that a standard silicon wafer can be used instead of the SOI wafer. In such a case, the silicon wafer would not have the buried oxide 4 used in the structure of FIG. 1.

Figure 2:
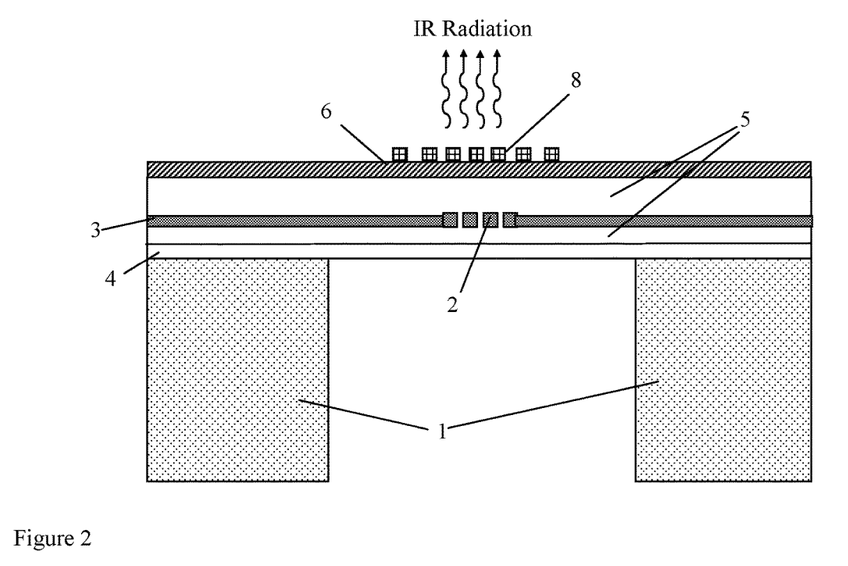
FIG. 2 illustrates a schematic cross-section of an alternative micro-hotplate made in an SOI process with a post processed plasmonic structure for use as an IR emitter, where the plasmonic structure is used to enhance the emission.

FIG. 2 shows another embodiment of the invention where the device is an IR emitter and has plasmonic structures 8 made of either gold or platinum on the top surface to enhance the IR emission of the device. These structures, 8 are done in a similar manner with the electrodes 7 shown in FIG. 1.

Figure 3:
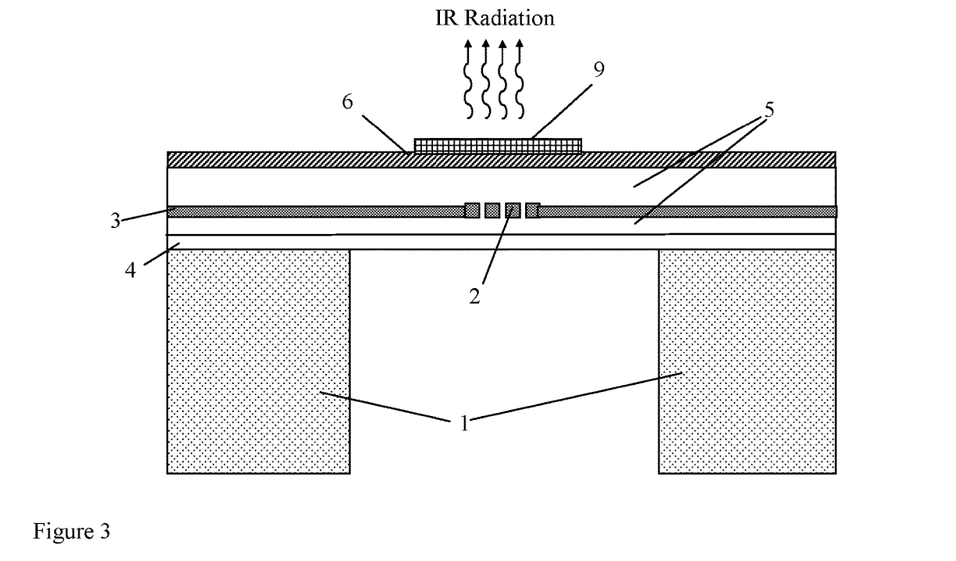
FIG. 3 illustrates a schematic cross-section of an alternative micro-hotplate made in an SOI process for use as an IR emitter with to top metal deposited as a sheet during post-processing to increase the emissivity of the emitter.

FIG. 3 shows an IR emitter where the top metal layer of gold or platinum is used to form a coating 9 that enhances the IR emission of the device.

Figure 4:
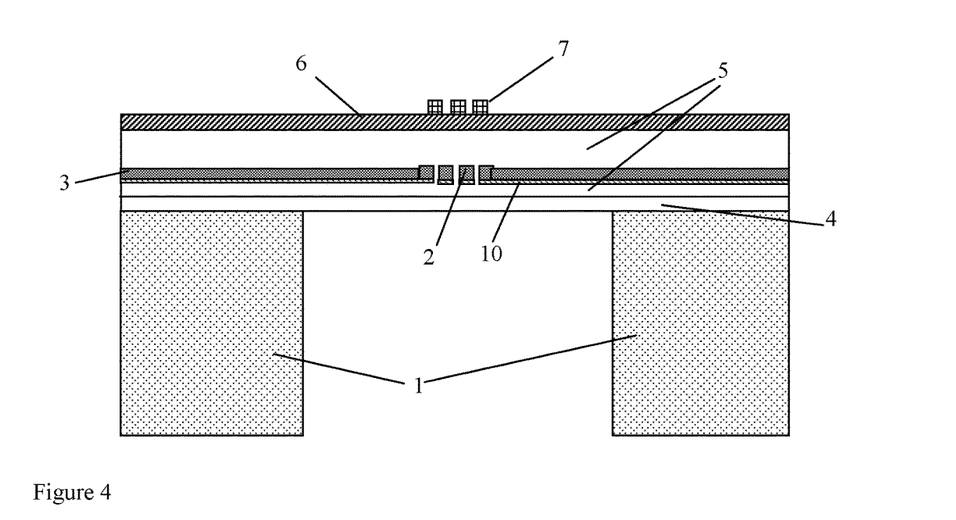
FIG. 4 illustrates a schematic cross-section of an alternative micro-hotplate made in SOI process with post processed electrodes for resistive gas sensing. The heater has a further adhesion layer added to the heater material to improve the adhesion and reliability of the heater.

FIG. 4 shows a micro-hotplate with post processed electrodes for resistive gas sensing. In this device, the heater has an additional layer 10 below the metal layer to improve the adhesion and the stability of the heater. It would be apparent that the additional layer 10 can also be applied to the heater if it is used in an IR emitter device.

Figure 5:
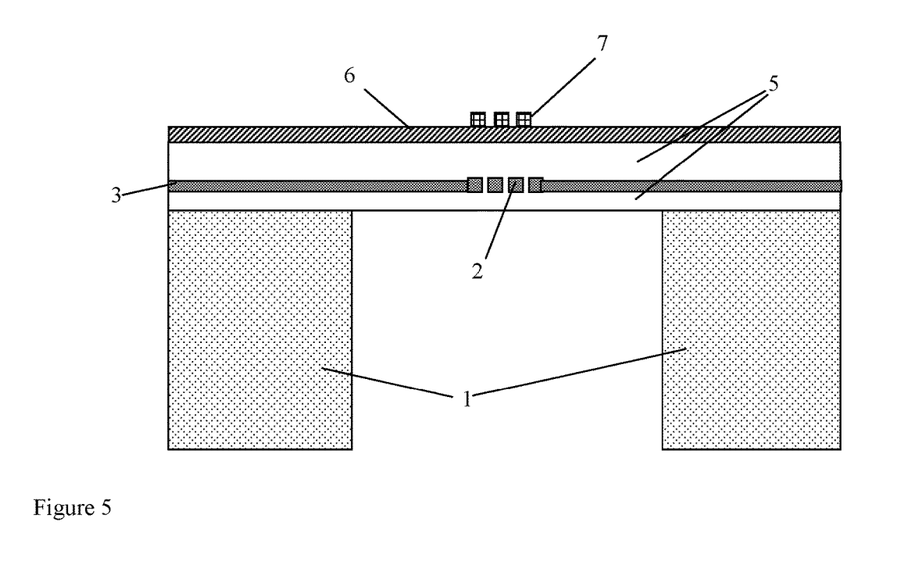
FIG. 5 illustrates a schematic cross-section of an alternative micro-hotplate made in a CMOS process with a starting bulk wafer with post processed electrodes for resistive gas sensing.

FIG. 5 shows a micro-hotplate with post processed electrodes for resistive gas sensing, fabricated using a process where the starting substrate was a bulk silicon substrate. In such a device, the buried oxide layer is not present.

Figure 6:
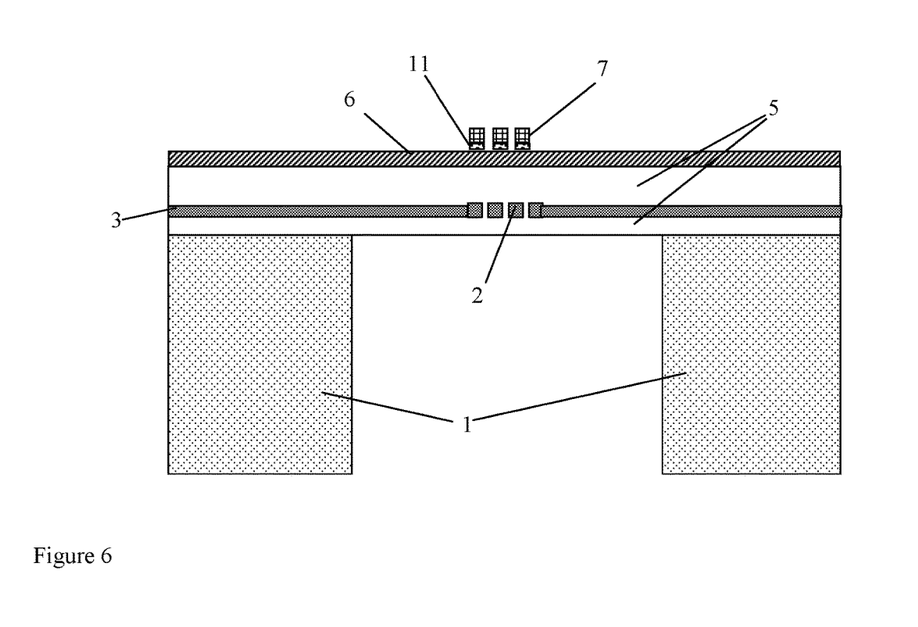
FIG. 6 illustrates a schematic cross-section of an alternative micro-hotplate made in a CMOS process with a starting bulk wafer with post processed electrodes for resistive gas sensing, where a layer is deposited just below the surface metal to improve the adhesion to the top surface, and/or reduce/prevent diffusion into the top surface.

FIG. 6 shows a micro-hotplate device, where the post processed electrodes have an additional layer 11 below them. This layer is to improve the adhesion of the metal (which can be gold or platinum) to the passivation. This layer maybe made from any material, or maybe a metal such as chromium, nickel or titanium, or can be more than one material layer.

Figure 7:
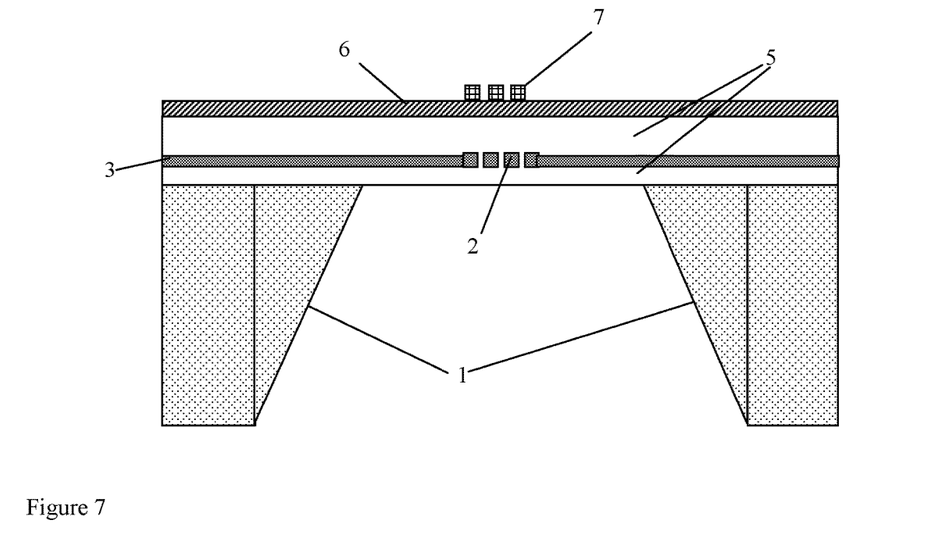
FIG. 7 illustrates a schematic cross-section of an alternative micro-hotplate made in a CMOS process with post processed electrodes, where the back etching is done by KOH etching.

FIG. 7 shows a micro-hotplate device with post processed electrodes, where the back etching has been perform by wet etching (for example using KOH or TMAH). This results in slanting sidewalls of the trench, as opposed to the vertical sidewalls created by DRIE.

Figure 8:
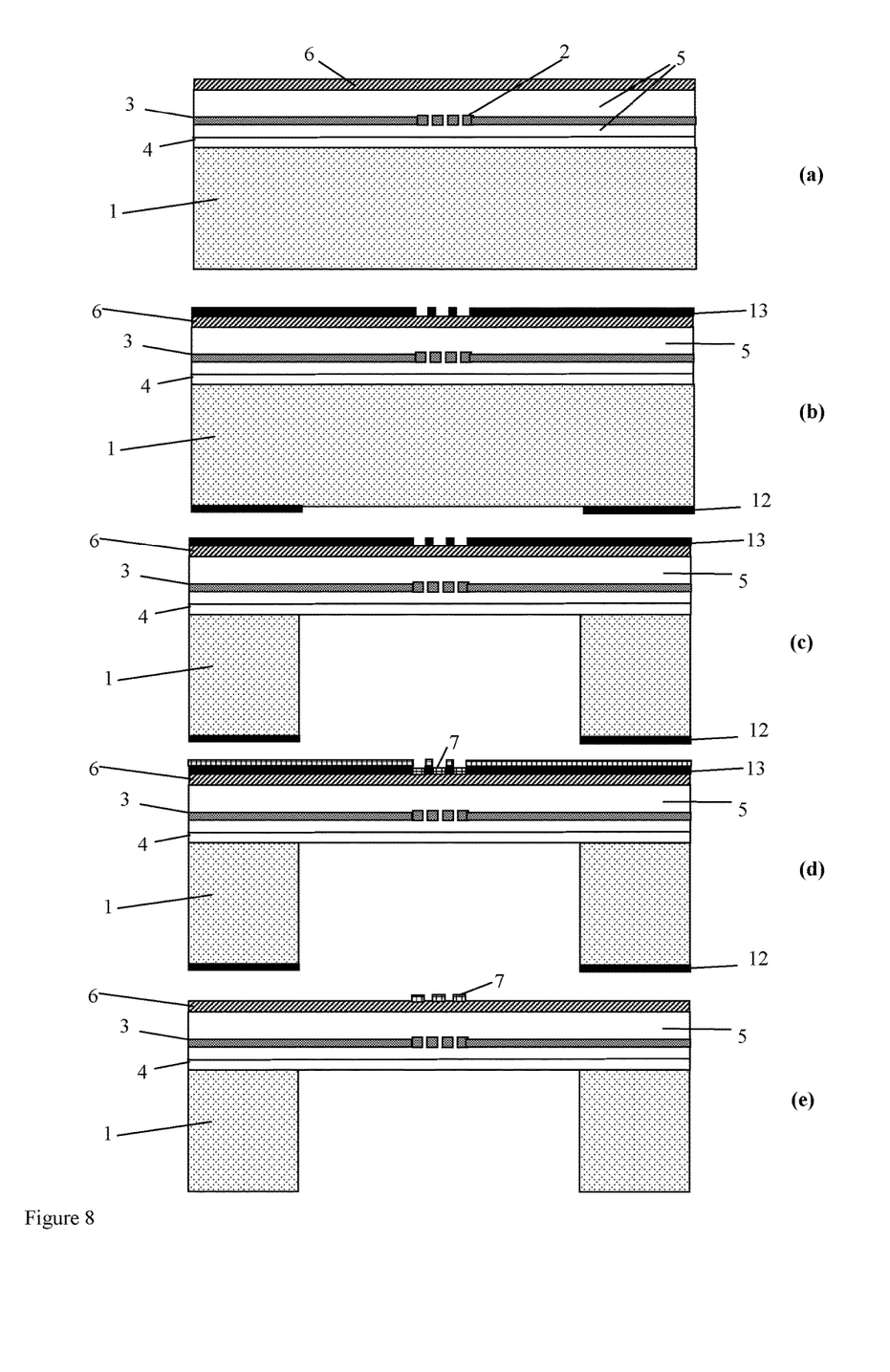
FIG. 8 shows the steps of the proposed method to deposit post processed Interdigitated electrodes (IDEs) on top of an SOI micro-hotplate.

FIG. 8 shows the main process involved in the deposition of the top metal layer structure of gold or tungsten. After the CMOS processing, the device is as shown in (a)

(a) It consists of a silicon substrate 1, a buried oxide layer 4, a heater 2 and tracks 3, dielectric oxide 5 and passivation 6. All these layers are formed within the CMOS sequence.

(b) Then a front side lithography mask 13 and a back side lithography mask 12 is spun and patterned on the front and back side of the wafer. This is one of the last steps of the CMOS sequence and defines the pattern of the future metal 7 that is done in step (d).

(c) The device is subsequently back etched using preferably a DRIE method.

(d) The top metal layer 7 (gold or platinum) is then deposited onto the device using sputtering or evaporation. If needed, one or more layers are deposited before the deposition of the final metal layer (gold or platinum) to improve the metal adhesion to the passivation surface and avoid diffusion into the oxide or passivation layers below.

(e) The photoresist done in step (b) is then removed together with unwanted parts of the top metal layer (gold or platinum).

It will be understood that the semiconductor structure of FIG. 1 (*a*) is manufactured using the standard CMOS process. One example of the detailed CMOS manufacturing steps is described as follows:

For the CMOS part of the process to form a simple metal heater (only steps relevant to the fabrication of a simple micro-hotplate are given):

1. The starting substrate is a silicon or an SOI wafer.
2. (only for the case of a starting SOI wafer) Patterning and defining the thin silicon layers, and having oxide in the rest. For the micro-hotplate area the design would typically replace the thin silicon with oxide. However, several other patterns are possible
3. A layer of dielectric 5 (silicon dioxide or silicon nitride) is deposited across the whole chip (micro-hotplate are and any circuitry).
4. A patterned metal layer is deposited. This forms the heater 2 within the micro-hotplate area.
5. Another layer of dielectric is deposited on top of the heater 2.
6. Another metal layer is deposited. This can optionally be used to form a plate or some other pattern above the heater.
7. Another layer of dielectric is deposited.
8. Another metal layer is deposited. This can optionally be used to form a plate or some other pattern above the heater.
9. A passivation layer 6 of silicon dioxide and/or silicon nitride is deposited.

It will be appreciated that this gives only one sequence of steps, and many other variations are possible and will be obvious to one well versed in the art. The CMOS process may contain other steps (such as p well and/or n well doping, polysilicon deposition, high p+ and n+ doping etc. to form a MOSFET)—for a simple device these will not have an effect in the micro-hotplate region, but maybe used to fabricate circuitry on the same chip. The process may also have a different number of metal layers.

Additionally, by varying the use of different layers, the heater can be made of either single crystal silicon (p doped or n doped), or of polysilicon (p doped or n doped), or of one of the other metal layers. The metal layers may have one or more layers or a different material above or below it to improve adhesion and reliability. The device may also have a diode or a resistive temperature sensor made of single crystal silicon, polysilicon or a metal layer.

Figure 9:
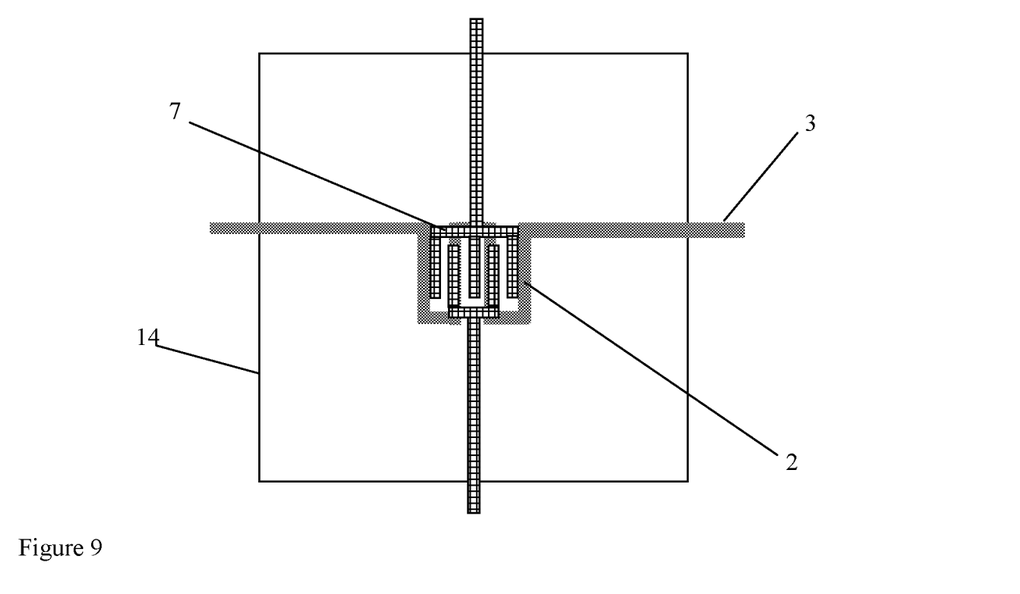
FIG. 9 shows a top view of a square micro-hotplate with post processed IDEs.
Figure 10:
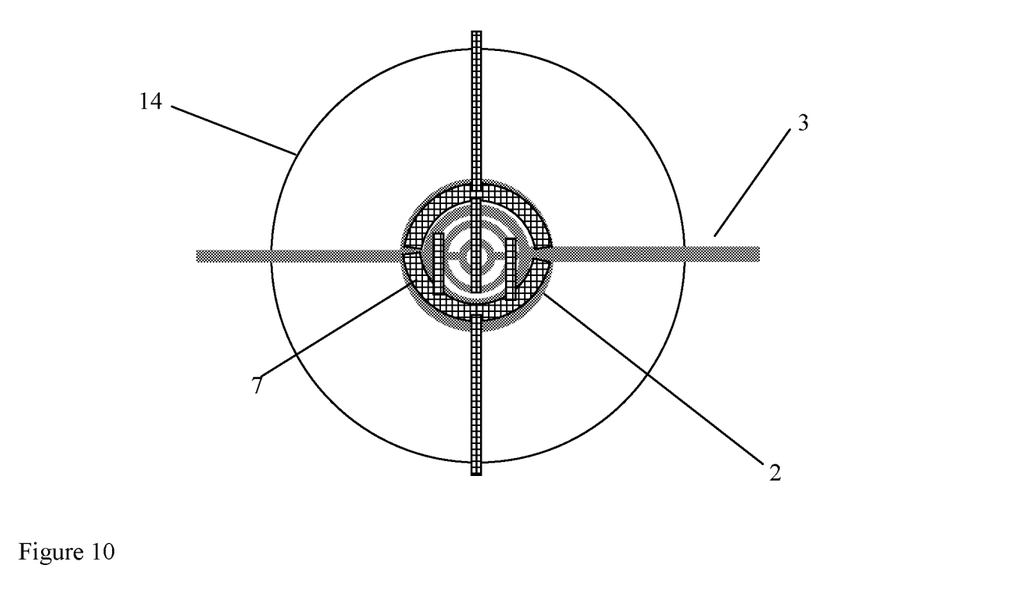
FIG. 10 shows a top view of a circular micro-hotplate with post processed IDEs.

FIG. 9 shows the top view of a micro-hotplate with interdigitated electrodes for resistive gas sensing. It has a rectangular membrane 14, and the electrodes are interdigitated. FIG. 10 shows a similar structure, but one where the membrane, heater and electrodes are circular.

Figure 11:
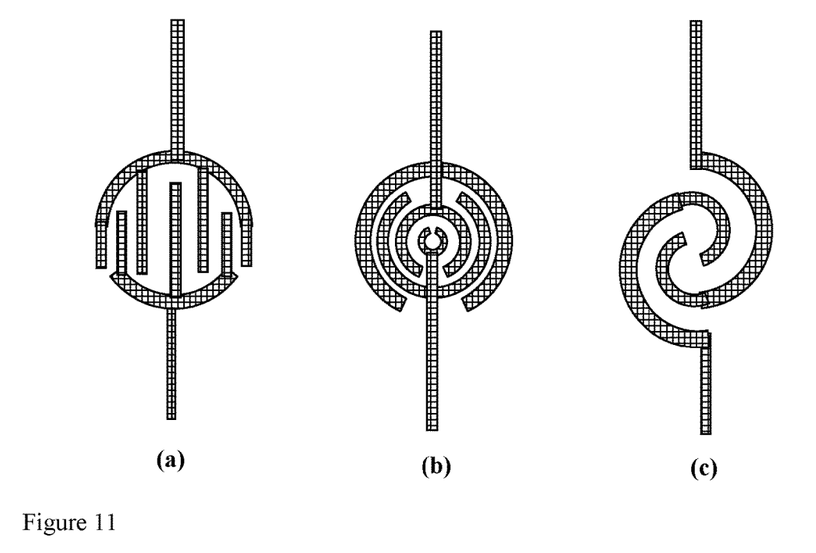
FIG. 11 shows a top view of some possible designs of electrodes for measuring the resistance of the sensing material on resistive gas sensors.

FIG. 11 shows some different shapes for electrodes used for resistive gas sensing. (a) shows a circular interdigitated shape. (b) shows interdigitated concentric rings. (c) shows electrodes in a spiral shape. Many other different shapes are possible. In particular, the electrodes can be rectangular in shape, or can be just 2 electrodes side by side. This figure shows only a few possible examples, and to one versed in the art many different shapes are possible.

Figure 12:
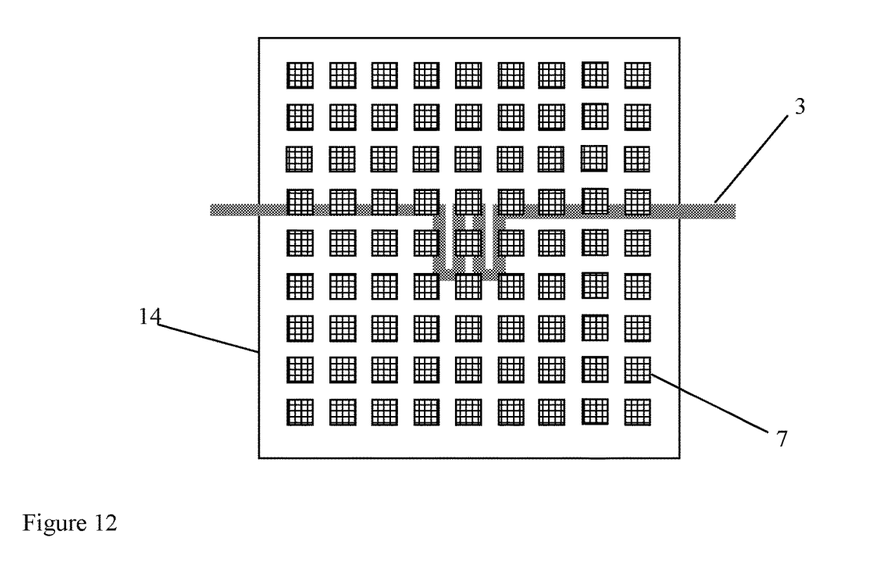
FIG. 12 shows a top view of an IR emitter with plasmonic structures deposited on it.

FIG. 12 shows the top view of an IR emitter with plasmonic structures formed of gold or platinum to enhance the emission. The figure shows these structures to be rectangular, however they maybe circular, triangular or trapezoidal shaped, or indeed any shape depending on the required emission spectral profile.

Figure 13:
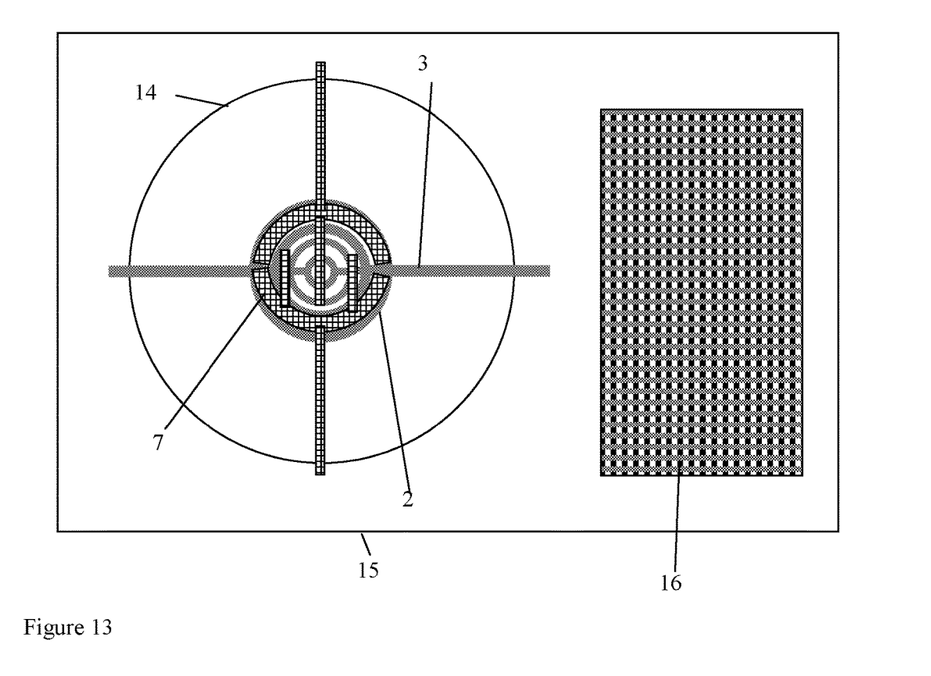
FIG. 13 shows the top view of a CMOS chip with micro-hotplates based gas sensors and interface circuitry on the same chip.

FIG. 13 shows the top view of a chip 15 with a micro-hotplate device and circuitry 16 on the same chip. This is made possible by the use of CMOS processing, allowing both the sensor device and circuitry to be on the same chip. The use of a CMOS compatible post processing method allows the top metal layers of gold or platinum to be deposited on the membrane.

Figure 14:
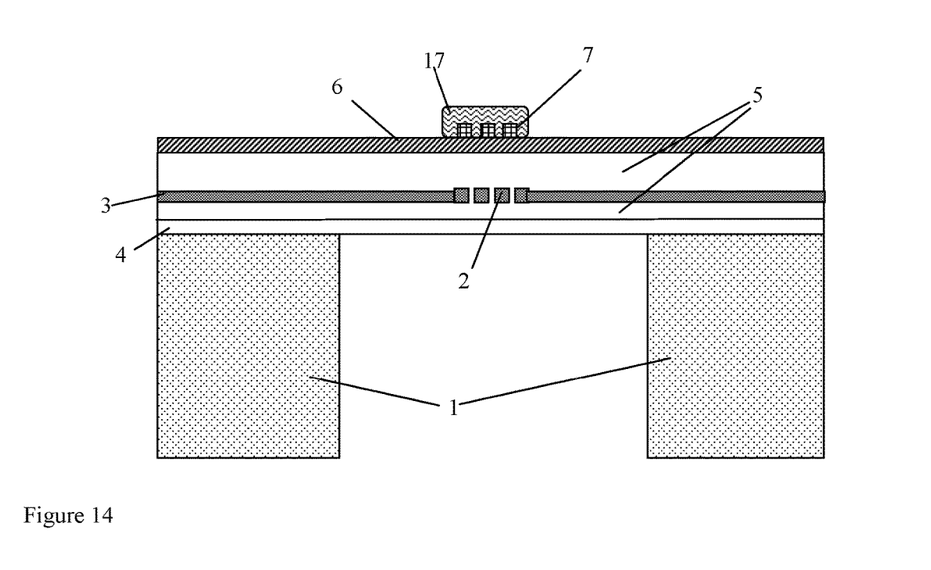
FIG. 14 illustrates a schematic cross-section of a micro-hotplate made in a CMOS SOI process with post processed electrodes for resistive gas sensing, and a chemical or gas sensing layer deposited as a drop layer.

FIG. 14 shows the schematic cross-section of a micro-hotplate made in an SOI process with post processed electrodes for resistive gas sensing. The device has a chemical or gas sensing layer 17 deposited on the metal electrodes 7. The sensing material is like a drop on the metal electrodes.

Figure 15:
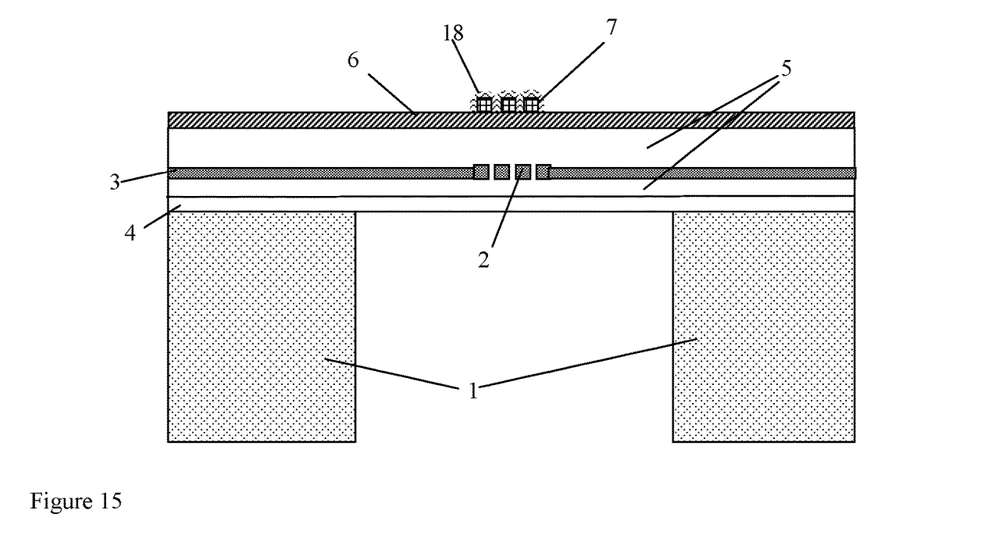
FIG. 15 illustrates a schematic cross-section of a micro-hotplate made in a CMOS SOI process with post processed electrodes for resistive gas sensing, and a chemical or gas sensing layer deposited as a conformal coating.

FIG. 15 shows the schematic cross-section of a micro-hotplate made in an SOI process with post processed electrodes for resistive gas sensing. The device has a chemical or gas sensing layer 18 deposited on the metal electrodes 7. The sensing material is coated conformally over the electrodes.

It will be appreciated that the process/method of the present invention can also be used to manufacture arrays of microhotplates. It is possible that the arrays are made on different membranes or have more than one microhotplate on a single membrane. For example, the proposed method can make a membrane with 4 heaters and 4 electrodes spaced laterally, or 4 membranes with 1 heater and 1 electrodes each.

The skilled person will understand that in the preceding description and appended claims, positional terms such as 'above', 'below', 'front', 'back', 'vertical', 'underneath' etc. are made with reference to conceptual illustrations of a semiconductor device, such as those showing standard cross-sectional perspectives and those shown in the appended drawings. These terms are used for ease of reference but are not intended to be of limiting nature. These terms are therefore to be understood as referring to a semiconductor device when in an orientation as shown in the accompanying drawings.

Although the invention has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the invention, whether alone or in any appropriate combination with any other feature disclosed or illustrated herein.

The invention claimed is:

1. A method of manufacturing a microhotplate comprising a semiconductor substrate, a dielectric region over the semiconductor substrate, a resistive heater within the dielectric region, the method comprising:

forming the semiconductor substrate, the dielectric region and the resistive heater using complementary metal oxide semiconductor (CMOS) compatible processing steps;
depositing a photo-resist material over the dielectric region using the CMOS compatible processing steps;
patterning the photo-resist material to form a patterned region over the dielectric region using the CMOS compatible processing steps;
etching at least a portion of the semiconductor substrate to form a dielectric membrane, wherein the steps of depositing the photo-resist material, patterning the photo-resist material and etching the portion of the semiconductor substrate are performed in sequence; and
wherein, after the etching of the semiconductor substrate, the method further comprises, depositing a metal structure in the patterned region over the dielectric region using a further process, wherein the further process is not a CMOS compatible process.

2. A method according to claim 1, wherein the steps of forming the semiconductor substrate, the dielectric region and the resistive heater, and the steps of depositing and patterning the photoresist material are performed within the CMOS compatible processing steps.

3. A method according claim 1, wherein said further process comprises at least one of depositing the metal structure by applying a sputtering or evaporation technique or depositing the metal structure both in the patterned region and on top of the photo-resist material.

4. A method according to claim 3, wherein said further process comprises removing the photo-resist material and the part of the metal structure on top of the photoresist material so that the metal structure formed in the patterned region is retained over the dielectric region, and optionally the photo-resist material and the part of the metal structure on top of the photo-resist material are removed using a chemical solution or a chemical solvent, and/or the photoresist material and the part of the metal structure on top of the photo-resist material are removed using a lift-off technique.

5. A method according to claim 1, wherein the step of patterning the photo-resist material comprises at least one of applying a mask to define the patterned region over the dielectric layer or using a photolithography technique within the CMOS compatible processing steps to define the patterned region over the dielectric region.

6. A method according to claim 1, wherein the step of etching the semiconductor substrate comprises applying a mask adjacent the semiconductor substrate to define the portion of the semiconductor substrate to be etched.

7. A method according to claim 1, wherein the step of etching the semiconductor substrate comprises one of:
applying a Deep Reactive Ion Etching (DRIE) technique; or
applying a wet etching technique, preferably using potassium hydroxide (KOH) or tetramethyl ammonium hydroxide (TMAH).

8. A method according to claim 1, wherein the resistive heater comprises a material selected from a group comprising tungsten, titanium, aluminum, polysilicon and single crystal silicon, and/or
further comprising forming a first barrier layer adjacent the resistive heater within the dielectric region.

9. A method according to claim 1, wherein, after the etching of the substrate and prior to depositing the metal structures, the method further comprises depositing a second diffusion barrier or adhesive layer on top of the photoresist region and in the patterned region over the dielectric region, optionally wherein the second diffusion barrier or adhesive layer comprises one or more material selected from a group comprising titanium, nickel and chromium.

10. A method according to claim 1, further comprising patterning the metal structure into one or more shapes selected from a group comprising:
(1) interdigitated electrodes
(2) electrodes arranged in shapes of concentric rings
(3) spiral shaped electrodes, and
(4) only two electrodes next to one another.

11. A method according to claim 1, further comprising at least one of:
patterning the metal structure into a series of dots or holes; or
depositing a gas sensitive layer on the metal structure, and optionally wherein the gas sensitive layer comprises a pure or doped metal oxide material selected from a group comprising tin oxide, tungsten oxide and zinc oxide.

12. A method according to claim 11, wherein the gas sensitive layer comprises a material selected from a group comprising polymers, nanowires, nanorods, nanoparticles and nano-plates.

13. A method according to claim 11, wherein the gas sensitive layer is a porous layer and/or a nanostructured layer.

14. A method according to claim 11, wherein the gas sensitive layer at least one of is deposited using a technique selected from a group comprising screen printing, sputtering, chemical vapour deposition (CVD) ink-jet and drop coating, or has a drop or conformal shape.

15. A method according to claim 1, wherein the microhotplate is formed from a bulk silicon wafer or a silicon-on-insulator (SOI) wafer.

16. A method according to claim 1, further comprising at least one of:
forming a passivation layer on the dielectric region using the CMOS compatible processing steps, the metal structure being deposited on the passivation layer, wherein optionally the passivation layer comprises a material comprising silicon dioxide or silicon nitride;
forming a temperature sensor within the dielectric region using the CMOS compatible processing steps, wherein optionally the temperature sensor is selected from a group comprising a diode temperature sensor, and a single crystal silicon, polysilicon or metal resistive temperature sensor;
forming a heat spreading plate within the dielectric region using the CMOS compatible processing steps, and optionally the heat spreading plate comprises a material selected from a group comprising single crystal silicon, polysilicon and a metal; or
integrating CMOS circuitry on the same chip as the microhotplate using the CMOS compatible processing steps, and optionally further comprising integrating a temperature sensor outside the dielectric membrane and within the same chip.

17. A method according to claim 1, wherein at least one of the microhotplate has a circular or rectangular shape, the dielectric membrane has a circular or rectangular shape, or the metal structure comprises gold or platinum.

18. A microhotplate comprising:
a semiconductor substrate having an etched portion;
a dielectric region over the semiconductor substrate;
a resistive heater formed within the dielectric region; and a patterned metal layer formed over the dielectric region,
wherein the semiconductor substrate, the dielectric region, the resistive heater, the etched portion in the substrate and the patterned metal layer are formed using the method according to claim 1.

* * * * *